(12) United States Patent
Thiagarajan et al.

(10) Patent No.: US 8,509,881 B2
(45) Date of Patent: Aug. 13, 2013

(54) TRUE ECG MEASUREMENT DURING CARDIO PULMONARY RESUSCITATION BY ADAPTIVE PIECEWISE STITCHING ALGORITHM

(75) Inventors: Srikanth Thiagarajan, Tustin, CA (US); Prabodh Mathur, Laguna Niguel, CA (US)

(73) Assignee: Cardiac Science Corporation, Waukesha, WI (US)

( * ) Notice: Subject to any disclaimer, the term of this patent is extended or adjusted under 35 U.S.C. 154(b) by 268 days.

(21) Appl. No.: 12/611,679

(22) Filed: Nov. 3, 2009

(65) Prior Publication Data

US 2011/0105930 A1    May 5, 2011

(51) Int. Cl.
*A61B 5/04*    (2006.01)

(52) U.S. Cl.
USPC ........................................................ 600/509

(58) Field of Classification Search
USPC ........................................................ 600/509
See application file for complete search history.

(56) References Cited

U.S. PATENT DOCUMENTS

| | | | |
|---|---|---|---|
| 5,405,361 A | 4/1995 | Persson | |
| 5,474,574 A | 12/1995 | Payne et al. | |
| 5,588,439 A | 12/1996 | Hollub | |
| 5,589,639 A | 12/1996 | D'Antonio et al. | |
| 5,649,544 A * | 7/1997 | Feng | 600/509 |
| 5,704,365 A * | 1/1998 | Albrecht et al. | 600/515 |
| 5,762,068 A | 6/1998 | dePinto | |
| 5,999,845 A | 12/1999 | dePinto | |
| 6,041,250 A * | 3/2000 | dePinto | 600/509 |
| 6,125,299 A | 9/2000 | Groenke et al. | |
| 6,178,357 B1 | 1/2001 | Gliner et al. | |
| 6,246,907 B1 | 6/2001 | Lin et al. | |
| 6,289,243 B1 | 9/2001 | Lin et al. | |
| 6,306,107 B1 | 10/2001 | Myklebust et al. | |

(Continued)

FOREIGN PATENT DOCUMENTS

| | | |
|---|---|---|
| EP | 1157717 A1 | 11/2001 |
| EP | 1 491 176 A1 | 12/2004 |

(Continued)

OTHER PUBLICATIONS

European Search Report, European Publication No. EP2319409 Al, dated Mar. 31, 2011, 3 Pgs.

(Continued)

*Primary Examiner* — Christopher D Koharski
*Assistant Examiner* — Nadia Ahmad
(74) *Attorney, Agent, or Firm* — Patterson Thuente Pedersen, P.A.

(57) ABSTRACT

A method and apparatus utilizing a piecewise stitching adaptive algorithm (PSAA) to filter signal artifacts, such as those induced by cardiopulmonary resuscitation (CPR) from sensed signals in real-time. PSAA is a method of estimating artifact component present in a first signal that is highly correlated with a second signal. The PSAA may utilize autocorrelation and cross-correlation calculations to determine signal sample windows in the first and second signals. The PSAA may estimate a signal artifact in a primary signal segment based on the determined correlations between the primary signal and an artifact signal. The PSAA may remove the estimated signal artifact from the primary signal. In the absence of an artifact signal, PSAA is able to estimate artifacts in the first signal utilizing filters. The PSAA may be implemented in Automated External Defibrillators, Monitor Defibrillators or other devices capable sensing highly correlated signals such as, for example, ECG and CPR signals.

23 Claims, 13 Drawing Sheets

(56) References Cited

U.S. PATENT DOCUMENTS

| | | |
|---|---|---|
| 6,351,671 B1 | 2/2002 | Mcklebust et al. |
| 6,390,996 B1 | 5/2002 | Halperin et al. |
| 6,480,734 B1 | 11/2002 | Zhang et al. |
| 6,553,257 B2 | 4/2003 | Snyder et al. |
| 6,658,290 B1 | 12/2003 | Lin et al. |
| 6,807,442 B1 | 10/2004 | Myklebust et al. |
| 6,827,695 B2 | 12/2004 | Palazzolo et al. |
| 6,961,612 B2 | 11/2005 | Elghazzawi et al. |
| 6,983,183 B2 | 1/2006 | Thiagarajan et al. |
| 6,993,386 B2 | 1/2006 | Lin et al. |
| 7,039,457 B2 | 5/2006 | Young et al. |
| 7,122,014 B2 | 10/2006 | Palazzolo et al. |
| 7,272,441 B1 | 9/2007 | Chapman et al. |
| 7,295,871 B2 | 11/2007 | Halperin et al. |
| 7,308,304 B2 | 12/2007 | Hampton et al. |
| 7,310,553 B2 | 12/2007 | Freeman |
| 7,476,206 B2 | 1/2009 | Palazzolo et al. |
| 7,565,194 B2 | 7/2009 | Tan et al. |
| 7,567,837 B2 | 7/2009 | Weil et al. |
| 2004/0210171 A1 | 10/2004 | Palazzolo et al. |
| 2004/0210172 A1 | 10/2004 | Palazzolo et al. |
| 2005/0101889 A1 | 5/2005 | Freeman et al. |
| 2006/0009809 A1 | 1/2006 | Marcovecchio et al. |
| 2006/0116724 A1 | 6/2006 | Snyder |
| 2006/0122648 A1 | 6/2006 | Elghazzawi et al. |
| 2007/0213775 A1 | 9/2007 | Snyder |
| 2007/0276300 A1 | 11/2007 | Olson et al. |
| 2008/0114406 A1 | 5/2008 | Hampton et al. |
| 2008/0208070 A1 | 8/2008 | Snyder et al. |
| 2008/0312708 A1 | 12/2008 | Snyder |
| 2009/0112135 A1 | 4/2009 | Palazzolo et al. |
| 2009/0177106 A1 | 7/2009 | Ricke et al. |

FOREIGN PATENT DOCUMENTS

| | | |
|---|---|---|
| EP | 1859770 A1 | 11/2007 |
| WO | WO00/27464 A2 | 5/2000 |
| WO | WO 02/22017 A1 | 3/2002 |
| WO | WO 2006/015348 A2 | 2/2006 |
| WO | WO2006/085120 A1 | 8/2006 |
| WO | WO 2008/068694 A1 | 6/2008 |
| WO | WO 2009/059288 A1 | 5/2009 |

OTHER PUBLICATIONS

K. Rhineberger, K. Unterkofler, M. Baubin, A. Amann, Removing CPR Artifacts from the Ventricular Fibrillation ECG by Enhanced Adaptive Regression on Lagged Reference Signals, *Computers in Cardiology*, 2006; 33: pp. 617-620.

K. Rhineberger, M. Baubin, K. Unterkofler, A. Amann, *Removal of Resuscitation Artifacts from Ventricular Fibrillation ECG Signls Using Kalman Methods*, Source Unknown.

Sung Won Yoon, Hang Sik Shin, Se Dong Min, and Myoungho Lee, Adaptive motion artifacts reduction algorithm for ECG signal in textile wearable sensor, *IEICE Electronics Express*, vol. 4, No. 10, pp. 312-318.

Joar Eilevstjohn, Trygve Eftestol, Sven Ole Aase, Hedge Myklebust, John Hakon Husoy, Petter Andreas Steen, Feasitility of shock advice analysis during CPR though removal of CPR artefacts from human the human ECG, *Resuscitation*, 61 (2004), pp. 131-141.

Ronald D. Berger, James Palassolo, Henry Halperin, Rhythm discrimination during uninterrupted CPR using motion artifact reduction system, *Resuscitation*, 75 (2007), pp. 145-152.

Part 5: Electrical Therapies, Automated External Defibrillators, Defibrillation, Cardioversion, and Pacing, *Circulation*, 2005;112:IV-35-IV46.

Thomas D. Rea, Sachita Shah, Peter J. Kudenchuk, Michael K. Copass, Leonard A. Cobb, Automated External Defibrillators: To What Extent Does the Algorithm Delay CPR?, *Annals of Emergency Medicine*, vol. 46, No. 2, Aug. 2005.

Elisabete Aramendi, Sofia Ruiz de Gauna, Unai Irusta, Jesus Ruiz, M. Fe Acocha, Jose Miguel Ormaetxe, Detection of ventricular fibrillation in the presence of cardiopulmonary resuscitation artefacts, *Resuscitation*, 72 (2007), pp. 115-123.

Zoll AED PRO Semi Automated External Defibrillator with Manual override, *OnCall Medical Supplies*, Website printout dated Feb. 11, 2009, 1 Pg.

First Aid Supplies and Safety Products, *First Aid and Safety Onnline Inc.*, AED, Philips AED, Fr2 AED, Website printout dated Feb. 11, 2009, 2 Pgs.

Scott C. Douglas and Ricardo Losado, Adaptive filters in Matlab: From Novice to Expert, DSP Workshop, 2002, 6 Pgs.

Patrick S. Hamilton, A Comparison of Adaptive and Nonadaptive Filters for Reduction of Power Line Interference in the ECG, *IEEE Transactions on Biomedical Engineering*, vol. 43, No. 1, 1996, 5 Pgs.

Maurice G. Bellanger, Adaptive Digital Filters, Chapter 1, *Marcel Dekker, Inc*, New York, 1987, 23 Pgs.

Michel Givers, A 30-year Journey Through an Exciting Field, *IEEE Control Systems Magazine*, Dec. 2006, 13 Pgs.

Sen M. Kuo and Dennis R. Morgan, Active Noise Control: A Tutorial Overview, *Proceedings of the IEEE*, vol. 87, No. 6, Jun. 1999, 31 Pgs.

Simon Haykin, Adaptive Filters, *Signal Processing Magazine*, 1999, 6 Pgs.

Bernard Widrow, John R. Glover, John M. McCool, John Kaunitz, Charles S. Williams, Robert H. Hearn, James R. Zeidler, Eugene Dong, and Robert C. Goodlin, Adaptive Noise Cancelling: *Principles and Applications, Proceedings of the IEEE*, vol. 63, No. 12, Dec. 1975, 26 Pgs.

Bernard Widrow and Samuel D. Stearns, Adaptive Signal Processing, Adaptive Interference Canceling, Applications Part IV, Chap. 12, Prentice-Hall, Englewood Cliffs, NJ, pp. 302-337, 1985, 37 Pgs.

Paulo S. R. Diniz, Adaptive Filtering—Algorithms and Practical Implementation, Second Edition, Kluwer Academic Publishers, 2002, 23 Pgs.

\* cited by examiner

TRUE ECG MEASUREMENT DURING CARDIO PULMONARY RESUSCITATION BY ADAPTIVE PIECEWISE STITCHING ALGORITHM

TECHNICAL FIELD

The invention relates generally to the field of systems, methods and apparatuses for the processing of electrocardiogram (ECG) signals. More specifically, the invention related to systems, methods and apparatuses for the adaptive reduction of artifacts in ECG signals caused by cardio pulmonary resuscitation (CPR).

BACKGROUND OF THE INVENTION

Nearly two decades have passed since Automatic External Defibrillators (AEDs) were created to help reduce incidents of cardiac arrest. Over that time, AEDs have become more prevalent in public locales such as offices, shopping centers stadiums and other areas of high pedestrian traffic. The AEDs empower citizens to provide medical help during cardiac emergencies in public places where help was previously unavailable in the crucial early stages of a cardiac event. In recent years, fully automated external defibrillators capable of accurately detecting ventricular arrhythmia and non-shockable supraventricular arrhythmia, such as those described in U.S. Pat. No. 5,474,574 to Payne et al., were developed to treat unattended patients. These devices treat victims suffering from ventricular arrhythmias and have high sensitivity and specificity in detecting shockable arrhythmias in real-time. Further, AEDs have been developed to serve as diagnostic monitoring devices that can automatically provide therapy in hospital settings as exhibited in U.S. Pat. No. 6,658,290 to Lin et al.

In addition to advances in the field of AEDs, there have been several advancements in the understanding of human physiology and how it relates to medical care. These advancements in medical research have lead to the development of new protocols and standard operating procedures in dealing with incidents of physical trauma. For example, in public access protocols for defibrillation, recent guidelines have emphasized the need for cardio-pulmonary resuscitation (CPR) along with use of AEDs. In fact, recent American Heart Association (AHA) Guidelines for Cardiopulmonary Resuscitation and Emergency Cardiovascular Care suggest that AEDs may be further integrated into emergency response protocols by detecting shockable rhythms, applying a shock and then prompting the rescuer to resume compressions immediately. (American Heart Association Guidelines for Cardiopulmonary Resuscitation and Emergency Cardiovascular Care, IV-36, American Heart Association, Inc., 2005). Further, the guidelines comment that AEDs may be developed that further retrain or assist the rescuer in direction, specifically reducing the number of withheld compressions due to reassessment of the patient and ensuring efficient transfer to trained medical professionals. The guidelines, along with independent research, led to an inclusive approach involving defibrillation, along with CPR, as the suggested method for AED device use.

Current AEDs, while providing defibrillation, are not functional in implementing the current suggested methods of AED use as recommended by the guidelines. Most of the AEDs available today attempt to classify ventricular rhythms. Specifically, current AEDs attempt to distinguish between shockable ventricular rhythms and all other rhythms that are non-shockable. This detection and analysis of ventricular rhythms requires real-time analysis of ECG waveforms. Thus, the functionality, accuracy and speed of the AED heavily depend on the algorithms and hardware utilized for real time analysis of ECG waveforms.

In many implementations, the algorithms depend on heart rate calculations and a variety of morphology features derived from ECG waveforms, like ECG waveform factor and irregularity as disclosed in U.S. Pat. No. 5,474,574 to Payne et al. and U.S. Pat. No. 6,480,734 to Zhang et al. Further, in order to provide sufficient processing capability, current AEDs commonly embed the algorithms and control logic into microcontollers.

It has been noted, that current algorithmic and specific hardware implementations can have a profound impact on the effectiveness of the AED. Specifically, the signal-to-noise ratio of ECG signals greatly effects AED performance. For example, during a rescue operation, algorithms implemented in many current AEDs require a few seconds of clean ECG signal data to classify a sensed ventricular rhythm. During cardiopulmonary resuscitation where a rescuer may apply chest compressions and relaxations, at a prescribed rate, close to 100 cycles per minute, the chances of obtaining such clean signal data are significantly reduced. In practice, the chest compressions and relaxations introducing significant motion artifacts in an ECG recording. In addition, ECG signals exhibit poor amplitudes during ventricular arrhythmia events, further reducing signal-to-noise ratios, often resulting in low quality or unusable signals. In these conditions, existing arrhythmia recognition algorithms may not perform adequately, leaving afflicted persons at risk.

Attempts have been made to reduce the effect of sensory artifacts by altering the designs of ECG electrodes and the analog front-end circuitry. One design implements a lower cut-off frequency for the high pass cut-off in ECG amplifiers. Other designs utilize differential amplifiers with very high common mode rejection ratio (CMRR) to attempt to avoid artifacts to an extent. However, in these designs it is essential to capture a good quality signal in the digital domain in order to remove any artifacts using digital logic and algorithms. This is mainly due to the fact that signal quantity lost as a result of saturation effects during analog to digital conversion is not recoverable using current known techniques.

In addition to the designs of electrodes, the current algorithms are not effective in artifact filtering under current standards and practices for CPR. One of the present challenges is to identify a shockable cardiac rhythm even during CPR compression cycles and to identify non-shockable/recovery rhythms in real-time. Because asystole condition is an important metric another challenge is to accurately detect asystole. Various methods for the identification and removal of CPR artifacts that can corrupt an ECG signal have been proposed. For instance, U.S. Pat. No. 6,961,612 utilizes a reference signal in attempting to remove artifacts. U.S. Pat. No. 7,039,457 provides an algorithm that relies on assumptions as to the operation of the cardiac system, along with a reference signal. U.S. Pat. No. 6,807,442, uses multiple sensors as indicators of CPR activity and to provide reference signals. U.S. Pat. No. 6,961,612 utilizes a reference signal indicative of CPR activity to identify the presence of CPR artifacts in an ECG segment. WO/2006/015348 discloses utilizing a transthoracic impedance measurement to identify significant patient motion. U.S. Pat. No. 5,704,365 describes utilizing a plurality of ECG leads to estimate the effect of noise on ECG signals. U.S. Pat. No. 7,295,871 discloses a frequency domain approach to system identification using linear predictive filtering and recursive least squares. In some recent research, K. Rhineberger introduced an alternative method of ECG filtering based on adaptive regression on lagged reference signals (Rheinberger, et al., Removal of resuscitation artifacts from ventricular fibrillation ECG signals using kalman methods, Computers in Cardiology (2005)). Still other methods of CPR artifact detection and filtering focus on utilizing frequency modulation instead of a reference signal to remove anomalies. (See Aramendi et al., Detection of ventricular fibrillation in the presence of cardiopulmonary resuscitation artifacts, Resuscitation (2007)). Other disclosed methods of implementing care in response situations focus on the detection and determination of CPR activity and utilize chest compression detectors (EP 1859770 A1) or accelerometers (U.S. Pat. No. 7,122,014) to estimate the depth and presence of CPR compressions.

However, all of these platforms or methods have limitations and concerns when providing real time care under recent American Heart Association CPR guidelines. Thus, a method and apparatus for filtering CPR artifacts from ECG signals that is effective over the diverse range of ECG segments, is computationally inexpensive and exhibits near real-time analysis and filtering thus enabling a clean ECG signal for determining shockable and non-shockable states is desired.

SUMMARY OF THE INVENTION

Various embodiments of the invention disclose a method and apparatus for filtering signal artifacts from a sensed ECG signal in real time. Various embodiments include devices or automated methods that utilize a piecewise stitching adaptive algorithm for filtering signal artifacts from an ECG signal. Various embodiments implement the piecewise stitching adaptive algorithm in computer hardware such as a specifically designed computer processor or microprocessor. Other embodiments store the piecewise stitching adaptive algorithm on a non-volatile computer-accessible memory. In various embodiments, the hardware is connected to sensors that sense physiological signals. In certain embodiments one of the sensors senses ECG signals. In other embodiments other sensors sense artifact signals. Artifact signals may be CPR compression signals, hemodynamic signals, or other signals reflective of additional physiological function that may produce artifacts in the ECG signal. Further, CPR artifact representative signals can be acquired using sensing techniques like ultrasounds, optical sensing and ballistocardiogram that can be indicative of physical origins of artifacts The method and apparatus may then execute the piecewise stitching adaptive algorithm to remove the artifact created by the artifact signal from the ECG signal by selecting signal sample windows from the ECG signal and artifact signal. Then primary signal and secondary signal segments may be generated from the ECG signal and the artifact signal. A relationship between the primary and secondary signal segments may then be determined which will allow for the estimation of a signal artifact in the primary signal based on the determined relationship. Finally, various embodiments may remove the estimated signal artifact from the primary signal segment.

In various embodiments, a rhythm analysis algorithm may be utilized to identify shockable ECG rhythm. This may allow the method and system to be utilized in medical devices such as Automated External Defibrillators (AED). The rhythm analysis algorithm may allow for the administration of life-sustaining therapy that complies with recent procedures, practices, and guidelines for CPR.

In various embodiments, the method and apparatus will optimize the filtering and sensing by only implementing the artifact filtering process when an artifact signal is sensed. In this way, required power and latency of therapy application is reduced. In other embodiments, signal sample windows are selected from ECG signal and artifact signal in uniform and non-uniform sized signal sample windows depending on the time delay between the ECG signal and the artifact signal. Thus, the method and apparatus may handle delays in sensing due to sensory deficiency as well as delays resulting from differences in physiology. In certain embodiments the start times and end times of the signal segments in the ECG and artifact signal will match. In other embodiments, the ECG signal and artifact signal sample window start and end times will be determined by utilizing an adaptive indexing or segment by segment regression schemes.

In various embodiments, the piecewise stitching adaptive algorithm will estimate the phase lead or phase lag between the ECG signal and artifact signal using a shifted autocorrelation calculation. These estimates may then be stored in memory for future use in selecting additional signal sample windows. In various embodiments the piecewise stitching adaptive algorithm utilized weighting schemes to apply weights to the primary and secondary signal segments. In certain embodiments, all segments are weighed equally. In other embodiments central segment weighting is utilized to provide more weight to the central signal segments.

In various embodiments, the method and apparatus may sense artifacts generated in other signals indicative of other physiological processes. Thus, in certain embodiments the artifact signal is a measure of hemodynamic activity. Further, the method and apparatus may utilize passive or active filtering on the primary signal in providing the artifact signal. Thus, in certain embodiments the ECG signal is filtered using a bandpass filter to provide the artifact signal. In these embodiments, the method and apparatus needs only one sensed signal in order to filter the signal artifacts.

DETAILED DESCRIPTION OF THE PREFERRED EMBODIMENTS

Figure 1:
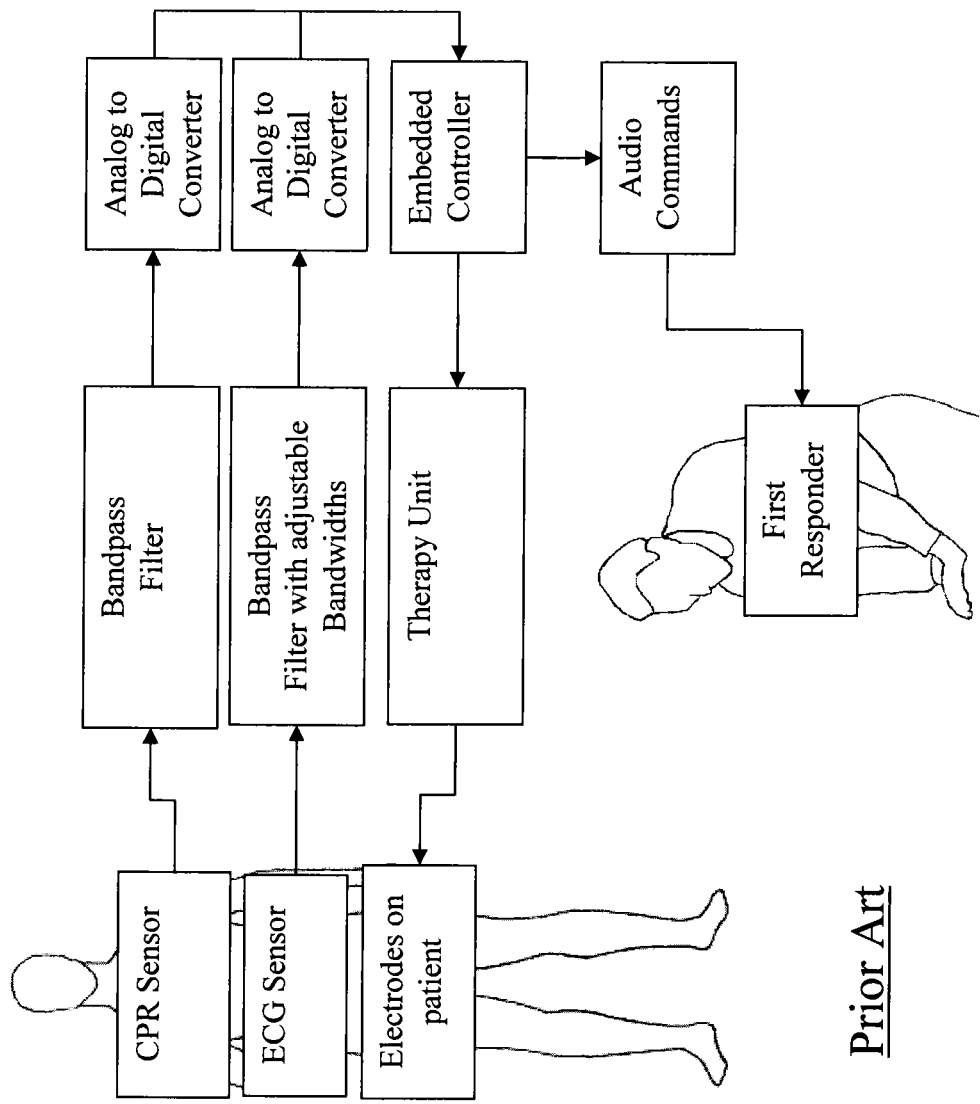
FIG. 1 is a schematic representation of an Automatic External Defibrillator.

As mentioned in the background, several algorithms have been implemented in current AEDs in an attempt to meet the revised AHA Guidelines for Cardiopulmonary Resuscitation and Emergency Cardiovascular Care. One implementation is the adaptive filter technology, which is briefly reviewed here in relation to a general schematic of an AED incorporating such algorithm as provided in FIG. 1.

While adaptive filters may be implemented utilizing several algorithms, Least Mean Square (LMS) algorithm, and its derivatives, is utilized most often. In a LMS adaptive filter, a mean square cost function is assumed (i.e.) $\xi=E[e^2(n)]$. The adaptive filter then minimizes the instantaneous squared error, $\xi(n)$, using the steepest gradient algorithm. This algorithm, updates the coefficient vector in the negative gradient direction with step size $\mu$. For example, in case of a FIR adaptive filter you have:

$$w(n+1)=w(n)-\mu 2 \cdot \nabla \xi(n) \quad (A)$$

where weights $w(n)$ can be adjusted every sample. Another algorithm utilized in many adaptive algorithms is the Recursive Least Square (RLS) algorithm. In an RLS algorithm, the cost function is given by:

$$\xi^d(k) = \sum_{i=0}^{k} \lambda^{k-i} e^2(i) = \sum_{i=0}^{k} \lambda^{k-i} [d(i) - x^T(i)w(k)] \quad (B)$$

Computationally, an update to the values of $\{w(n)\}$ has to be done for every sample for both LMS and RLS based adaptive filters. These computations are very costly and multiple computations are needed for every update. Further, there are no ways to adjust the computations being done to every sample in every window. Additionally, adaptive algorithms have a settling time and the settling time for minimum error output or usable signal (noise removed) takes several seconds. Settling time also depends on initial values of weights and parameters $\lambda$ for RLS algorithm and $\mu$ for LMS algorithm.

In a CPR artifact removal problem, time varying nature of ECG and CPR signals add complexity to the adaptive process. ECG signals vary from Ventricular Tachycardia (VT) to Ventricular Fibrillation (VF), fine Ventricular Fibrillation and asystole. Further recovery signals also vary from asystole to fine VF, VT, supraventricular tachycardia (SVT) and so on. The frequency and amplitudes of all these waveforms show enormous variations within themselves. On top of these variations, CPR artifacts such as compressions and expansions vary widely between rescue personnel and also during a particular cycle of CPR. Further, actual amplitudes of compressions and expansions vary widely. Essentially, the variability of ventricular signals, mated with CPR artifacts precludes the adaptive filter from settling, reducing operational capacity of the device that implements this approach.

With this understanding of the capabilities and insufficiencies of adaptive filter techniques present today, embodiments of the invention will now be described.

Other embodiments provide a solution to denoising ECG signal using a piecewise stitching adaptive algorithm (PSAA). In various embodiments, the PSAA may utilize piecewise regression and/or piecewise deconvolution methods in order to effectively analyze and clean a sensed ventricular signal.

In various embodiments, the PSAA utilizes a reference signal received from devices that measure CPR activity. These embodiments allow the PSAA to have a baseline or reference of all CPR activity, which can then be used to correlate the CPR activity with the sensed ECG. The acquisition methodology, origin, sampling technique, filtering methods and sensors utilized in obtaining the CPR signal mirrors what is utilized in obtaining ECG signals. For example, common mode ECG may be utilized in determining the CPR reference signal in order to insure proper representation of CPR activity. By utilizing the same techniques, the CPR reference signal many be mapped one-to-one with the ECG signal reference, resulting in an instantaneous correlation of the CPR data with the ECG data. Other embodiments may utilize reference signals generated from sensing mechanical acceleration, velocity, or distance measurements. However, in utilizing these alternative reference signals, accuracy may decline due to possible causal relationships between the reference signal and the artifact component of the ECG. Thus, embodiments may utilize the time series CPR reference signal along with the time series ECG to promote accuracy.

While utilizing the same methodology in measuring CPR reference signals and ECG signals promotes accuracy, the sensed signals still may not align one-to-one within a sample frame. This may be due, in part, to the propagation of mechanical or electrical signals through various body tissues. For example conduction through muscle cells may create a distortion in the signals. In other situations, the methods utilized in sensing the ECG and CPR signal may differ slightly due to differences in sensory devices or other system requirements. These differences, however slight, may also introduce delay, resulting in the lack of a one-to-one correlation. Various embodiments may utilize convolution or transfer functions to assist in determining the relationship between the CPR signal and the ECG signal. This allows for the correlation of multiple samples in one time series to the other. For example, a segment of more than one sample in an artifact component of ECG signal can be related to a similar sized segment in a CPR reference signal. Once established, the relationship between the CPR reference signal and the ECG signal may be utilized to remove artifacts from the ECG signals. In various embodiments, both instantaneous demixing and deconvolution algorithms are utilized in removing CPR artifacts from the ECG signal.

In order to understand the invention, some discussion of the various signals and overarching principals in ECG and CPR signaling must be discussed. After understanding these principals and how they relate, further appreciation of the various embodiments of the invention may be realized.

Signals such as ECG signals, artifact component signals affecting ECG signals and reference signals are considered to be stochastic (or) random signals. Such signals cannot be reproduced at will. Major statistical parameters representing a stochastic signal are its mean, variance, and autocovariance.

Practical signal processing or time series estimations are possible only when the signals exhibit ergodicity. A stochastic signal is defined to be an ergodic signal if all its statistical properties can be estimated from a single realization of sufficiently large finite length. For ergodic signals, time averages equal ensemble averages derived via the expectation operator in the limit as the length of realization goes to infinity.

For a real ergodic signal, following are the estimation formula:

$$m_x = \lim_{M \to \infty} \frac{1}{2M+1} \sum_{n=-M}^{M} x[n] \quad (1)$$

$$\sigma_X^2 = \lim_{M \to \infty} \frac{1}{2M+1} \sum_{n=-M}^{M} (x[n] - m_x)^2 \quad (2)$$

$$\gamma_{XX}[l] = \lim_{M \to \infty} \frac{1}{2M+1} \sum_{n=-M}^{M} (x[n] - m_X)(x[n+l] - m_X) \quad (3)$$

Instead of above limiting operations, finite sums can be used as shown below.

$$\hat{m}_X = \frac{1}{M+1} \sum_{n=0}^{M} x[n] \quad (4)$$

$$\hat{\sigma}_X^2 = \frac{1}{M+1} \sum_{n=0}^{M} (x[n] - m_X)^2 \quad (5)$$

$$\hat{\gamma}_{XX}[l] = \frac{1}{M+1} \sum_{n=0}^{M} (x[n] - m_X)(x[n+l] - m_X) \quad (6)$$

For a random signal, autocorrelation (or) autocovariance functions play a very vital role. Suppose, if an ecg signal $\{ecg(n)\}$ is made of superposition of $\{s(n)\}$ and $\{r(n)\}$, $\{s(n)\}$ representing clean signal components and $\{r(n)\}$ is a random noise component, then its autocorrelation can be expressed as $$E(ecg[n]ecg[n+l]) = E\{(s[n] + r[n])(s[n+l] + r[n+l])\} = \quad (7)$$
$$E\{s[n]s[n+l]\} + E\{s[n]r[n+l]\} + E\{r[n]s[n+l]\} + E\{r[n]r[n+l]\}$$

Since $\{ecg[n]\}$ and $\{r[n]\}$ are uncorrelated, equation (7) reduces to $$E\{ecg[n]ecg[n+l]\} = E\{s[n]s[n+l]\} + \sigma_r^2 \quad (8)$$

Hence, autocorrelation preserves signal content, while restricting the random uncorrelated noise to a dc component, in many practical situations. Hence, autocorrelation and crosscorrelations are used in random signal estimation problems, to analyze a random signal characteristics and its interaction with another signal. This is better than using raw signals to analyze and estimate random signal characteristics.

With this understanding, an appreciation for the invention described herein can be realized. Let us assume an observed ECG signal, during Cardiopulmonary Resuscitation (CPR) as $\{y(n)\}$, made up of a combination of artifact component $\{a_1(n)\}$, along with ECG signal component $\{ecg(n)\}$ as indicated above and uncorrelated wide band noise $\{N_1(n)\}$. Let the CPR reference signal indicative of CPR activity be represented as $\{x(n)\}$. Mathematically, the relations can be expressed as:

$$\{y(n)\} = \{ecg(n)\} + \{a_1(n)\} + \{N_1(n)\}$$

$$\{x(n)\} = \{b(n)\} + \{a_2(n)\} + \{N_2(n)\} \quad (9)$$

As mentioned above, in various embodiments, $\{y(n)\}$ refers to ECG signal observed when recorded from automated external defibrillator electrodes, $\{ecg(n)\}$ indicates the true ECG component, $\{a_1(n)\}$ indicates the artifact component seen in the observed ECG, when CPR is performed. $\{N_1(n)\}$ and $\{N_2(n)\}$ indicate uncorrelated wide band noise, that is always present in any electronic sensor systems. When CPR is not performed, artifact component $\{a_1(n)\}$ should be zero. In other embodiments, $\{x(n)\}$ indicates the CPR reference signal, indicative of CPR activity and is made up of: a baseline activity component, $\{b(n)\}$, that should be very close to zero in all situations, the actual artifact signal, $\{a_2(n)\}$, recorded by CPR sensor and uncorrelated wide band noise $\{N_2(n)\}$. In various embodiments $\{x(n)\}$ is zero when CPR activity does not happen. Thus, in various embodiments, artifact $\{a_1(n)\}$ is estimated in $\{y(n)\}$, using $\{x(n)\}$ and removed, thus resulting in a clean ECG signal $\{ecg(n)\}$.

In various embodiments an additional constraint is to restrict the implementation of entire operation in a time domain. Windowing the data into multiple small windows provides an opportunity to implement a real-time algorithm, allowing the AED to perform this analysis in a live rescue operation.

$$E[x(n)x^T(n)] = R_{xx}(0) = \text{autocorrelation of } x \text{ and}$$

$$E[x(n)y^T(n)] = R_{xy}(0) = \text{cross-correlation between } y \text{ and } x \quad (10)$$

Expanding further above two relations, we arrive at $$R_{xx}(0) = \sum_{n=0}^{N-1} x(n)x(n) \text{ and} \quad (11)$$

$$R_{xy}(0) = \sum_{n=0}^{N-1} x(n)y(n)$$

In other words, above computations are a subset of computations leading to auto-correlation (ACS) and cross-correlation (CCS) sequences:

$$R_{xx}(l) = \frac{1}{M+1} \sum_{n=0}^{M} (x[n] - m_X)(x[n+l] - m_X) \text{ and} \quad (12)$$

$$R_{xy}(l) = \frac{1}{M+1} \sum_{n=0}^{M} (x[n] - m_X)(y[n+l] - m_Y)$$

Various embodiments utilize a stable linear time-invariant system (LTI) discrete-time system with an impulse response $\{h[n]\}$, that relates the CPR reference signal $\{x(n)\}$ with observed ECG signal $\{y(n)\}$. These embodiments define an input-output relation by:

$$y[n] = \sum_{k=-\infty}^{\infty} h[k]x[n-k] \quad (13)$$

Further, in these embodiments an assumption is made that the ACS as defined in equation (12) is known within the bounds of the immediate calculation. The result of the assumption is a CCS as shown in equation (12) being computed as:

$$r_{yx}[l] = \sum_{n=-\infty}^{\infty} y[n]x[n-l] \quad (14)$$

Substituting (13) in (14), we get $$r_{yx}[l] = \sum_{n=-\infty}^{\infty} \left( \sum_{k=-\infty}^{\infty} h[k]x[n-k] \right) x[n-l] = \quad (15)$$

$$\sum_{k=-\infty}^{\infty} h[k] \left( \sum_{n=-\infty}^{\infty} x[n-k]x[n-l] \right) = \sum_{k=-\infty}^{\infty} h[k]r_{xx}[l-k]$$

In various embodiments it is realistic to assume that the causal finite-length impulse response of length N and equation (15) reduces to:

$$r_{yx}[l] = \sum_{k=0}^{N-1} h[k]r_{xx}[l-k] \quad (16)$$

In this way, both ACS and CCS, $r_{xx}[l]$ and $r_{yx}[l]$, are computed. Then, given ACS and CCS, system identification (or) impulse response estimation is performed.

In various embodiments, a recursive relation for computing the impulse response samples $\{h[n]\}$ of the CPR reference signal $\{x[n]\}$ and the observed ECG signal $\{y[n]\}$ is given as equivalent to finding an impulse response samples $\{h[n]\}$ between ACS $\{r_{xx}[l]\}$ and CCS $\{r_{yx}[l]\}$. Utilizing ACS and CCS provide the same information as utilizing the CPR reference signal $\{x[n]\}$ and the observed ECG signal $\{y[n]\}$ but also have the added advantage of reducing the impact of uncorrelated noise on the observed ECG signal $\{y[n]\}$.

The following recursive computations help in computing impulse response samples $\{h[n]\}$ from the values of ACS $\{r_{xx}[l]\}$ and CCS $\{r_{yx}[l]\}$.

$$h[0] = \frac{r_{yx}[0]}{r_{xx}[0]} \text{ and } h[n] = \frac{r_{yx}[n] - \sum_{k=0}^{n-1} h[k]r_{xx}[n-k]}{r_{xx}[0]}, n \geq 1 \quad (17)$$

Thus, artifact $\{a_1[n]\}$ is estimated, or reconstructed, from the relation between CPR reference signal $\{x[n]\}$ and observed ECG signal $\{y[n]\}$. The artifact is then subtracted from the observed ECG signal $\{y[n]\}$ to get clean ECG signal $\{ecg[n]\}$, as indicated in the model shown in equation (9).

In various embodiments, overlapped windowing is used to create a continuous output signal $\{ecg[n]\}$, after the removal of estimated artifact due to CPR. Exact overlapping segments may be identified and contributions due to impulse responses $\{h_i[n]\}$, $\{h_{i+1}[n]\}$, etc. are weighed. Proper weighting ensures that there are no sudden jumps in the intermediate output, namely the reconstructed artifact component $\{a_1[n]\}$.

Figure 2:
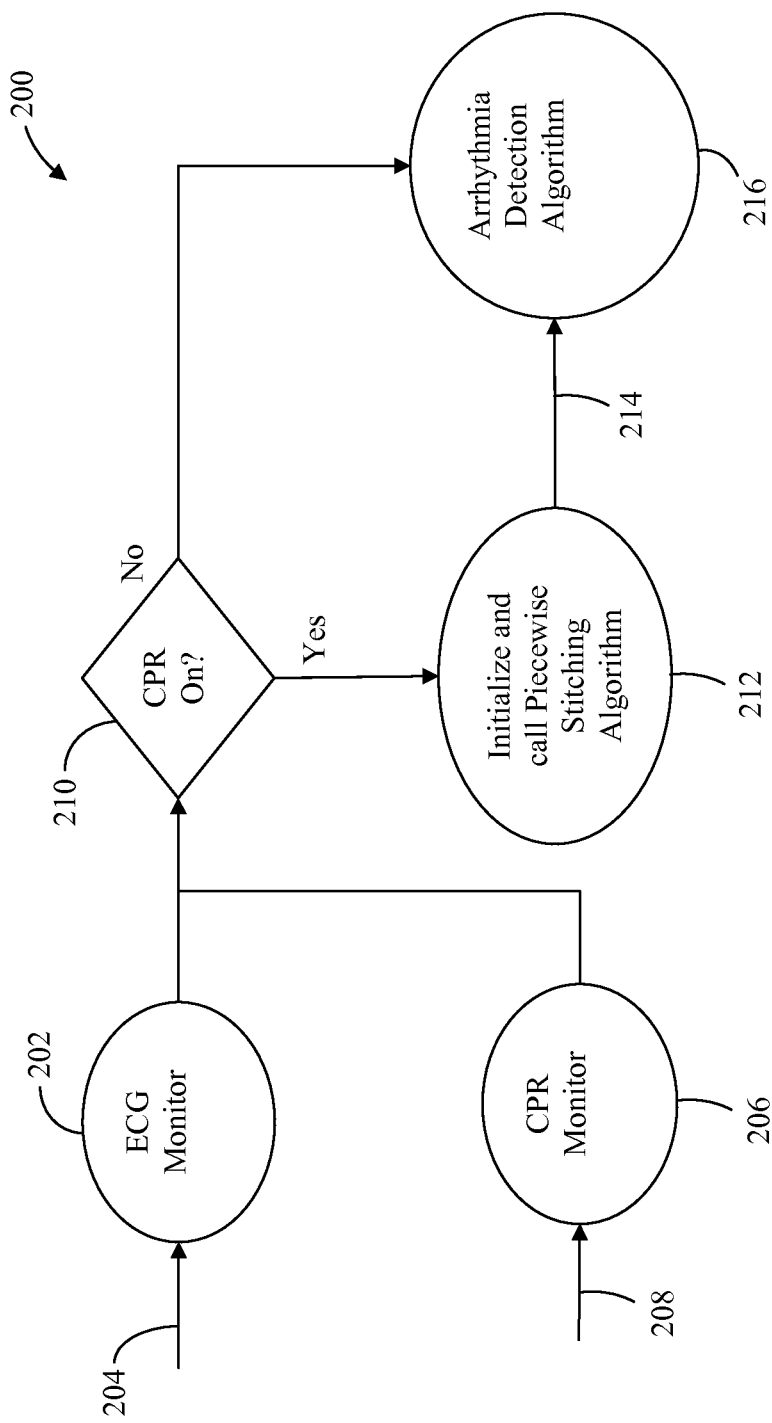
FIG. 2 is a schematic representation of an Automatic External Defibrillator utilizing the Piecewise Stitching Adaptive Algorithm according to one embodiment of the invention.

Referring to FIG. 2 an embodiment of a system 200 utilizing the PSAA is presented. In various embodiments, a system may utilize an ECG monitor 202 that receives an ECG signal 204. The ECG monitor 202 may monitor or record the ECG signal 204 from sensors placed on the body. The ECG monitor 202 may analyze the ECG signal 204 and condition it for further processing. Further, the ECG monitor 202 may identify anomalies or artifacts that are present due to additional actions being taken such as CPR compressions. Various embodiments will have a CPR monitor 206 that analyzes a CPR signal 208. The CPR signal 208 may provide an independent indication of CPR activity being performed. Further, the CPR monitor 206 may condition the CPR signal 204 for further processing. The system 200 may then utilize decision logic 210 to determine whether PSAA is required. If the logic 210 determines CPR signal 208 is present, it will initialize and call the PSAA algorithm 212. The PSAA algorithm 212 will then take the ECG signal 204 and the CPR signal 208 and remove the CPR signal 208 from the ECG signal 204 to provide an ECG signal 214 clean of CPR artifacts. The ECG signal 214 may then be passed to other algorithms of the system 200 such as an Arrhythmia Detection Algorithm 216. In certain embodiments, if the CPR signal 208 is not present, then the logic 210 will not initialize the PSAA algorithm 212 and the system 200 will pass the ECG signal 204 directly to the other algorithms such as an Arrhythmia Detection Algorithm 216.

Other embodiments may sense a variety of primary and secondary signals wherein the secondary signal provides additional data or signal input to the primary signal and is preferentially removed or filtered utilizing the PSAA. For example, motion artifacts in Stress ECG machines, respiratory artifacts in ECG and Stress ECG machines, machine artifacts in Stress ECG machines, electrooculagraphy signals in EEG, ECG signals/Pulse from EEG signals and CPR artifacts from other hemodynamic signals. In this way, various embodiments may remove artifacts in various signals representing physical impulses such as ECG, EEG, utilizing a second signal representing various physical impulses such as CPR compressions.

Figure 3:
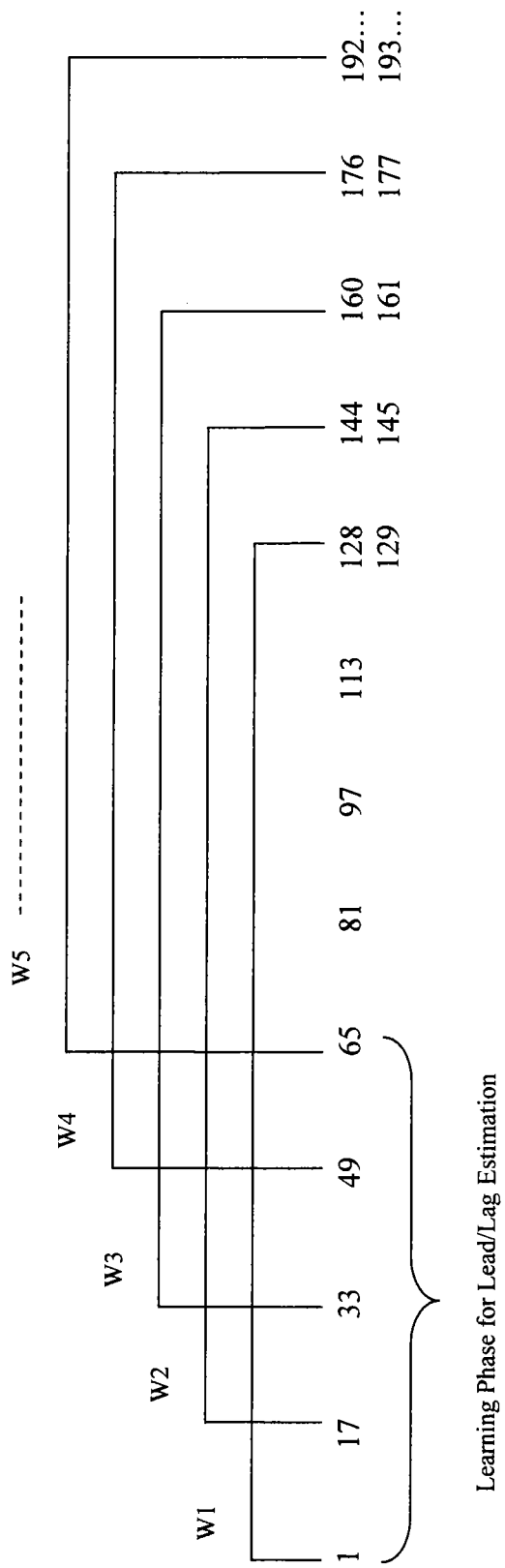
FIG. 3 is a graphical representation of the Piecewise Stitching Algorithm utilizing convolution according to one embodiment of the invention.

Referring to FIG. 3, an embodiment of the PSAA utilizing a convolution algorithm is presented. In various embodiments, the overlapping convolution output segments is implemented by first windowing the first $W_L$ samples of observed ECG signal $\{y[n]\}$ and CPR reference signal $\{x[n]\}$, where $W_L$ indicates the window length. A rectangular window is then applied on both the input signals to generate CPR reference signal segments $\{x_1(n)\}$ and observed ECG signal segments $\{y_1(n)\}$. This step is visualized in the following equation:

$$y_1(n) = \begin{cases} y(n)w(n), & 0 \leq n < W_L \\ 0, & \text{else} \end{cases} \quad (18)$$

$$x_1(n) = \begin{cases} x(n)w(n), & 0 \leq n < W_L \\ 0, & \text{else} \end{cases}$$

$R_{xy}(k)$ and $R_{xx}(k)$ values are then computed for lags up to $N_{lag}$ points wherein $N_{lag}$ is an measured indication of time lag between the observed ECG signal segment $\{y_1(n)\}$ and the CPR reference signal segment $\{x_1(n)\}$. The lead/lag and windows estimation is shown, for example, in FIG. 3. Next, CCS and ACS functions, are determined as given above in equation (12), after subtracting mean values of $\{y_1(n)\}$ and $\{x_1(n)\}$. Following the determination of CCS and ACS functions, $\{h(n)\}$ is determined from the relationship between the two using equation (17) and the size of $\{h(n)\}$ is set equal to $N_{lag}$. Next, the mean value is removed from CPR signal using the following equation:

$$m_0 = \text{mean}\{x_1[n]\}$$

$$\{x_1[n]\} = \{x_1[n]\} - \text{mean}\{x_1[n]\} = \{x_1[n]\} - m_0 \quad (19)$$

Then $\{h(n)\}$ is used to construct $\{x'_1(n)\}$, using the convolution formula shown below. $\{x'_1(n)\}$ is the estimated artifact.

$$x'_1(n) = \sum_{k=-\infty}^{\infty} h(k) x_1(n-k) \quad (20)$$

Length of signal $\{x'_1(n)\}$ is $W_L + N_{lag} - 1$.

The output of convolution $\{x'_1(n)\}$ is then truncated to the first $W_L$ points. Ideally, truncation should avoid beginning and ending $N_{lag}$ points. However, various embodiments just avoid $N_{lag} - 1$ points. Still other embodiments reduce the impact of initial $N_{lag}$ points by giving them lower weight in subsequent calculations of estimating the artifact. Next, the dc response of convolution operation is integrated, as shown in equation (21):

$$x'_1(n) = m_0 \times \sum_{k=0}^{N_{lag}-1} h(k) \quad (21)$$

wherein $m_0$ is the modulation depth of excitation in the modulation ratio M (equal to $m/m_0$). Next, estimate the artifact segment $\{a_1(n)\}$ on the data utilizing the equation provided in (22):

$$\{x^{out}(n)\}|_{n=0}^{n=N_{lag}-1} = x'_1(n)|_{n=0}^{n=N_{lag}-1} \quad (22)$$

In various embodiments, the output of the first non-overlapping segment between first and second windows is the same. Further, various embodiments assume that windows jump by $N_{lag}$ points. However, this jump may be determined by an input parameter or otherwise computed and indicated in $N_{jump}$. Following the determination of the artifact segment $\{a_1(n)\}$ the clean ECG signal $y^{est}$ may be estimated for the first $N_{lag}$ points.

$$\{y^{est}(n)\}|_{n=0}^{n=N_{lag}-1} = \{y(n)\}|_{n=0}^{n=N_{lag}-1} - \{x^{out}(n)\}|_{n=0}^{n=N_{lag}-1} \quad (23)$$

In case of constant lead or lag by a few points between CPR reference signal $\{x(n)\}$ and $\{y(n)\}$, shifted cross-correlation with $N_{lag}/2$ (or) $N_{lag}$ points in both segments will yield a maximum at particular lead of lag. Above subtraction is performed after shifting the estimated artifact signal $\{a_1(n)\}$ or $\{x^{out}(n)\}$ accordingly.

Next, move to new windowed segments $\{y_2(n)\}$ and $\{x_2(n)\}$, by jumping $N_{jump}$ points, between $N_{jump}$ and $(N_{jump} + W_L)$ samples. Then repeat prior steps utilizing the new window parameters.

In various embodiments, different weighting schemes may be utilized in estimating second, third and subsequent non-overlapping segments of data. These weighting schemas include: equal weighting and central segments weighting.

In an equal weighting scheme, an overlapped segment between two adjacent windows get calculated twice and so, equal weighting will be given to two adjacent window calculations, if only two windows overlap. Similar is the case for three adjacent computations, with a particular small segment being common to them. For example, if you set $N_{lag}/N_{jump}$ of 16 points and have $W_L$ of 128 points (i.e.), then a particular segment can be present in 8 neighboring windows. First segment of $N_{jump}$ (or) $N_{lag}$ points:

$$\{x^{out}(n)\}|_{n=0}^{n=N_{lag}-1} = x'_1(n)|_{n=0}^{n=N_{lag}-1} \quad (24)$$

Second segment of $N_{jump}$ (or) $N_{lag}$ points:

$$\{x^{out}(n)\}|_{n=N_{lag}}^{n=2*N_{lag}-1} = (x'_1(n)|_{n=N_{lag}}^{n=2*N_{lag}-1} + x'_2(n)|_{n=0}^{n=N_{lag}-1})/2 \quad (25)$$

Third segment of $N_{jump}$ (or) $N_{lag}$ points:

$$\{x^{out}(n)\}|_{n=2*N_{lag}}^{n=3*N_{lag}-1} = (x'_1(n)|_{n=2*N_{lag}}^{n=3*N_{lag}-1} + x'_2(n)|_{n=N_{lag}}^{n=2*N_{lag}-1} + x'_3(n)|_{n=0}^{n=N_{lag}-1})/3 \quad (26)$$

From eighth segment, all eight overlapping windows are available for computation. Thus, if the ratio $W_L : N_{lag} = 8:1$, each overlapping segment of $N_{lag}$ points gets computed eight times. In certain embodiments, there is a possibility of end-effects negatively impacting accuracy due to convolution impacting these calculations. Thus, embodiments remove the end-segments from consideration in windows, $W_L$, where the overlapping segments fall on the end.

Center heavy weighting in computation of segments common to neighboring windows is utilized as a weighting scheme, in various embodiments, for the PSAA. The center heavy weighting scheme eliminates uncertainty provided by the edges in convolution of a set of windows, $W_L$, by weighting the center segments. For example, if only six windows are utilized and a particular segment is present in the center, avoiding the windows on the two extremes and applying weight to the four windows in the center is center weighting. The center weighting algorithm is expressed as follows:

$$\{x^{out}(n)\}|_{n=k*N_{lag}}^{n=(k+1)*N_{lag}-1} = \frac{\text{Numerator } term1 + \text{Numerator } term2}{12} \quad (27)$$

Numerator $term1 =$ $$\left( x'_{(k+1)}(n)\Big|_{n=0}^{n=N_{lag}-1} + 2 * x'_k(n)\Big|_{n=N_{lag}}^{n=2*N_{lag}-1} + 3 * x'_{k-1}(n)\Big|_{n=2*N_{lag}}^{n=3*N_{lag}-1} \right)$$

and

Numerator $term2 = \left( 3 * x'_{(k-2)}(n)\Big|_{n=3*N_{lag}}^{n=4*N_{lag}-1} + 2 *\right.$ $$\left. x'_{(k-3)}(n)\Big|_{n=4*N_{lag}}^{n=5*N_{lag}-1} + x'_{k-4}(n)\Big|_{n=5*N_{lag}}^{n=6*N_{lag}-1} \right)$$

As a result of center weighting, various embodiments exhibit more stability in the convolution.

Figure 4:
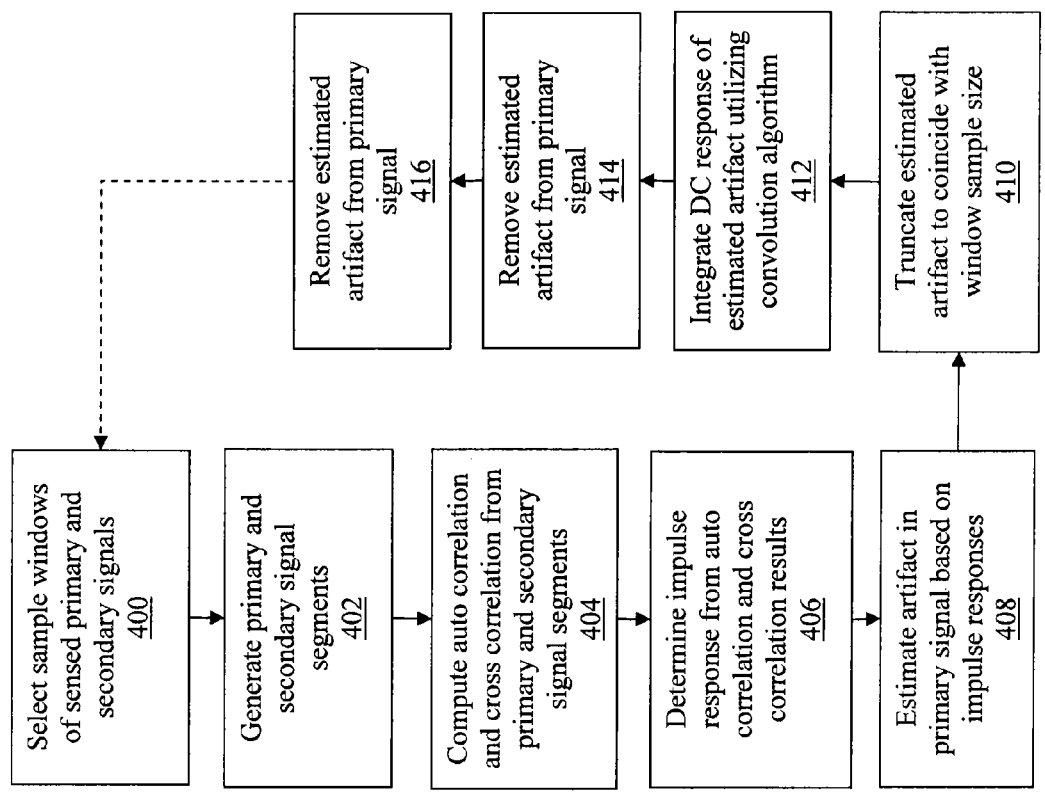
FIG. 4 is a flow chart depicting the operation of the Piecewise Stitching Algorithm utilizing convolution according to one embodiment of the invention.

Referring to FIG. 4, a system implementing the PSAA using the convolution algorithm according to one embodiment is presented. First select sample windows are selected from the primary and secondary observed signals 400. Next, the primary signal segments and the secondary signal segments are generated 402. The auto and cross correlations are then computed from the primary and secondary signal segments 404. Next the impulse responses are determined from the auto- and cross correlations 406. Then, the estimated artifact present in the primary signal is estimated from the impulse response 408. The estimated artifact is then truncated to coincide with the length of the selected primary and secondary signal sequences 410. Then, the DC response of the estimated artifact is integrated utilizing convolution 412. The estimated clean primary signal is generated by removing the estimated artifact from the selected primary signal 414. At this point, the cycle may repeat for the next selected sample windows of the primary and secondary signals. In this way, embodiments may filter the entire primary signal with a high degree of accuracy utilizing the PSAA and convolution algorithm.

Figure 5:
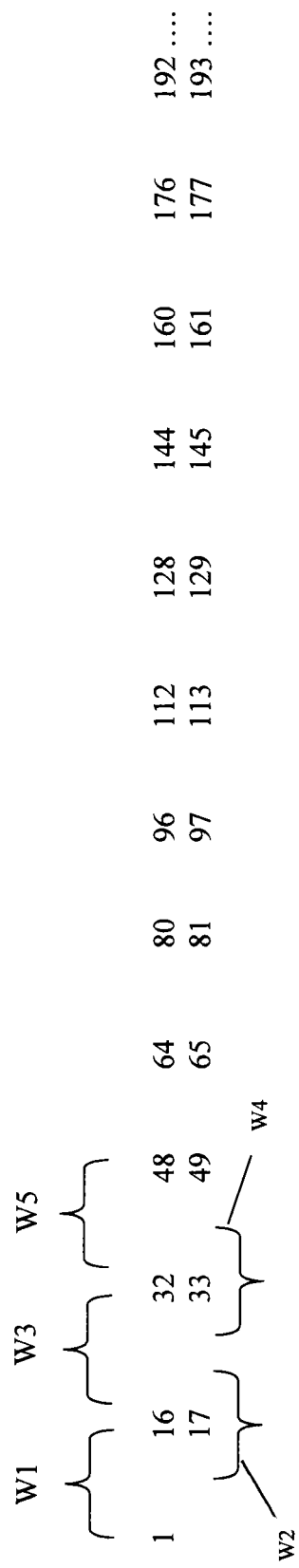
FIG. 5 is a graphical representation of the Piecewise Stitching Algorithm utilizing regression according to one embodiment of the invention.

Now referring to FIG. 5 an embodiment of the PSAA utilizing overlapping regression segments is presented. This embodiment is similar to window based overlapping convolution output segments, except that output segments are computed from a simple regression relation between $\{x(n)\}$ and $\{y(n)\}$. Assumption here is that the artifact and the reference signal have a point-by-point correlation, even if the relation is obscured by other components. In other words, relations are assumed to be piecewise linear.

In this embodiment, estimates of $\alpha$ and $\beta$ are made in every window of $W_L$ samples (~2 seconds), and windows are given overlaps of $W_L/2$ samples. Non-stationarity is accounted up to an extent, by this overlap. In each window, $\hat{\alpha}$ and $\hat{\beta}$ are calculated as per equation (30).

$$\hat{\alpha} = \frac{\sum_{i=0}^{L}(x(i)-m_x)(y(i)-m_y)}{\sum_{i=0}^{L}(x(i)-m_x)^2} \text{ and} \quad (30)$$

$$\hat{\beta} = \overline{y} - \hat{\alpha}\overline{x}$$

$$a_1'(n) = \hat{\alpha}x(n) + \hat{\beta} \quad (31)$$

$$\text{Clean signal estimate} = y(n) - a_1'(n) \quad (32)$$

Here, a linear regression equation was fit between $\{y(n)\}$ and $\{x(n)\}$ and an estimation of artifact component is made and is removed from observed ECG signal $\{y(n)\}$.

Estimates of $\hat{\alpha}$ and $\hat{\beta}$ in equation (30) may help to reconstruct the artifact component in observed, corrupted ECG signal, $\{y(n)\}$. Further, additional windowing and overlapping methods may be utilized to simulate the overlapping convolution scheme and can eliminate non-stationary issues. Additionally, using smaller segments allows non-stationarity of relations to be captured.

Figure 6:
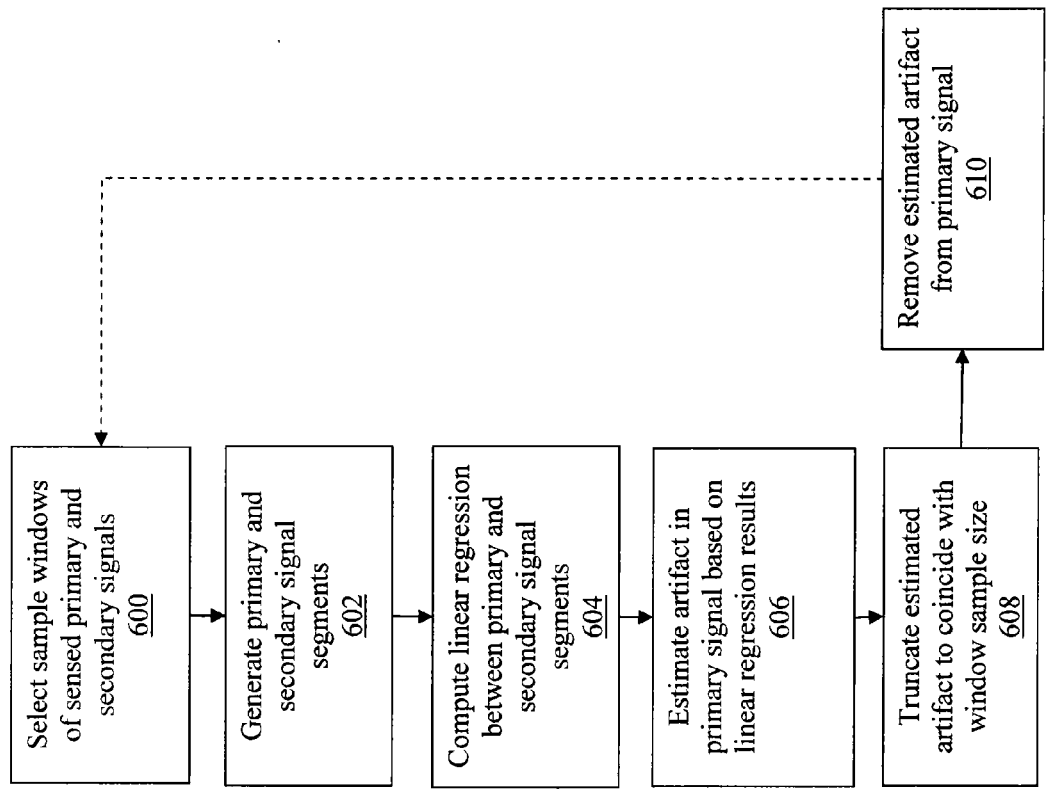
FIG. 6 is a flow chart depicting the operation of the Piecewise Stitching Algorithm utilizing regression according to one embodiment of the invention.

Referring to FIG. 6 an embodiment of the PSAA utilizing linear regression segments is presented. First, select sample windows are selected from the primary and secondary observed signals 600. Next, the primary signal sequence and the secondary signal sequence are generated 602. The linear regression is then determined between the primary and secondary signals 604. Next the estimated artifact is generated based on the linear regression 606. The estimated artifact is then truncated to coincide with the length of the selected primary and secondary signal sequences 608. The estimated clean primary signal is generated by removing the estimated artifact from the selected primary signal 610. At this point, the cycle may repeat for the next selected sample windows of the primary and secondary signals. In this way, various embodiments may filter the entire primary signal with a high degree of accuracy utilizing the PSAA and linear regression algorithm.

Figure 7:
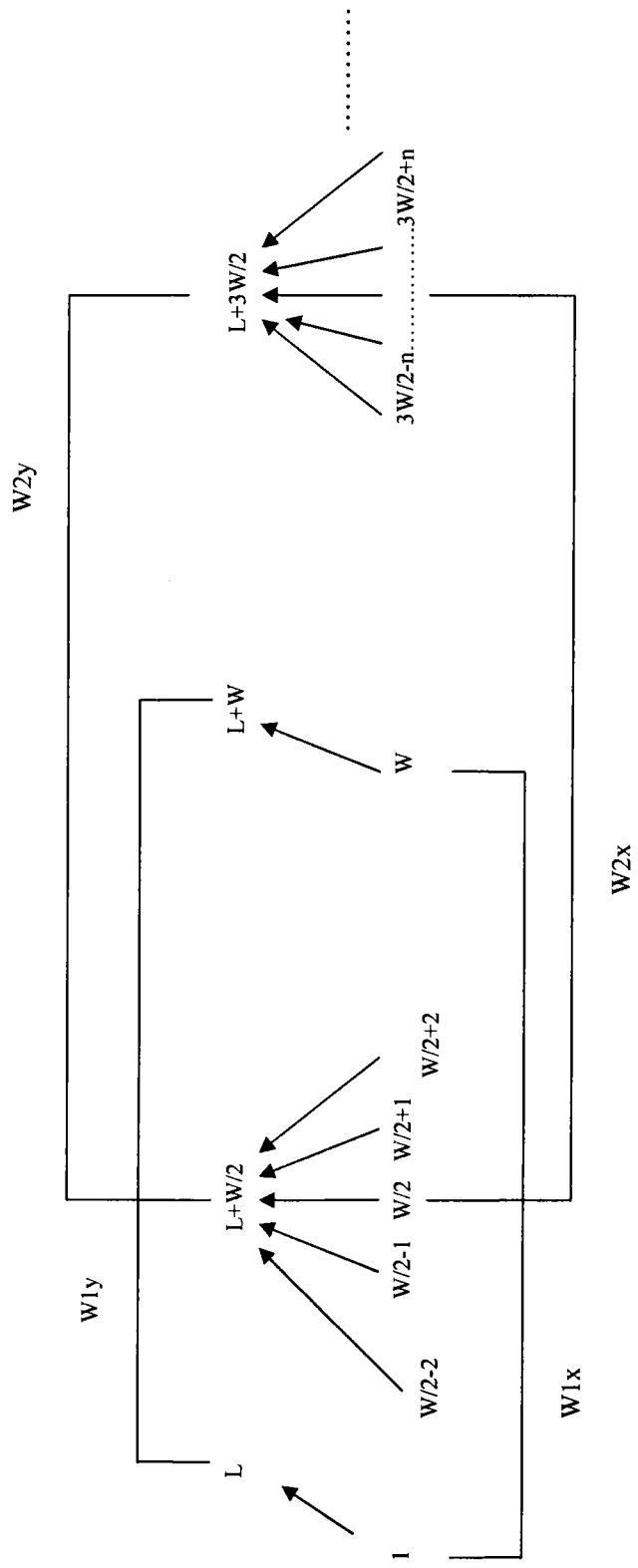
FIG. 7 is a graphical representation of the Piecewise Stitching Algorithm utilizing variable window regression according to one embodiment of the invention.

As shown in FIG. 7, a time varying, adaptive windowing scheme is also possible with piecewise regression implementation of PSAA scheme. In this set-up, overlap segment size, window start point in $\{x(n)\}$ and $\{y(n)\}$ all can change along with window size. This approach leads to segment-by-segment correlation, with segments that are unequal, with biases due to different number of computations per point. However, an acceptable artifact waveform can be built and can be subtracted from $\{y(n)\}$ for arriving at artifact-removed ECG signal.

In various embodiments, every signal sample, both in the sensed ECG signal and CPR reference signal, initiates computation and parameter storage actions. For example, computation of average, computation of auto-correlation sequence, cross-correlation sequences and the deconvolution and convolution operations happen continuously. However, in certain embodiments, additional computations such as the estimate the artifact segment are only performed at particular indices. In this way, the PSAA is able to reduce the amount of computation required in signal filtering and analysis.

Now referring to FIGS. 8A-8D various embodiments of systems utilizing the PSAA are presented. The embodiment depicted in 8A inputs the ECG signal 800 and the CPR reference signal 802 into the PSAA 804. The PSAA will then remove the CPR artifacts from the ECG signal 800 and provide the estimated actual ECG signal 806 for further use.

Figure 8A:
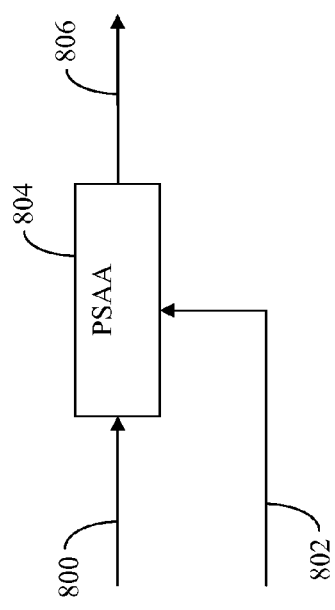
FIG. 8A is a schematic representation of an implementation of the Piecewise Stitching Algorithm according to one embodiment of the invention.
Figure 8B:
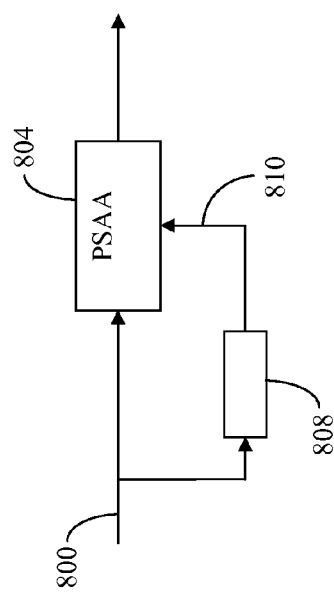
FIG. 8B is a schematic representation of an implementation of the Piecewise Stitching Algorithm according to one embodiment of the invention.

Referring to FIG. 8B, an embodiment of a system utilizing the PSAA without a reference signal is presented. In many cases, the low frequency region of the ECG signal 800 recorded during CPR is dominated by a CPR artifact. Thus, where there is no reference signal, filtering the ECG signal 800 utilizing a low pass filter 808 enables salient features of reference signal. Though not as accurate as exact CPR related signal, this low-pass filtered output signal 810 can be used as $\{x(n)\}$ in the PSAA 804. In various embodiments, processing delay is minimized or made linear by using finite impulse response (FIR) filters. Lead or lag computation may utilize correlation analysis and subsequently applied. In various embodiments the low pass filter filters select signal ranges, for example, between (0-6) Hz.

Figure 8C:
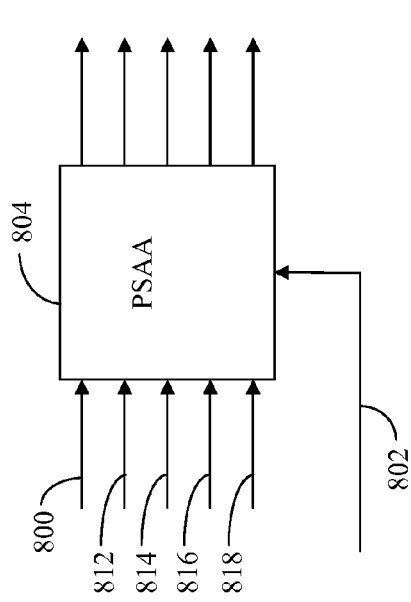
FIG. 8C is a schematic representation of an implementation of the Piecewise Stitching Algorithm according to one embodiment of the invention.

Referring to FIG. 8C various embodiments may utilize the PSAA 804 to clean CPR artifacts from several input signals artifacts from several input signals using CPR reference signal 802. Input signals may include: ECG signal 800, $pO_2$ signal 812, atrial blood pressure (ABP) signal 814, central venous pressure (CVP) signal 816, and the heart sound signal 818. In this way, the PSAA 804 may filter the CPR artifact from multiple signals concurrently and provide uncorrupted signals for further analysis.

Figure 8D:
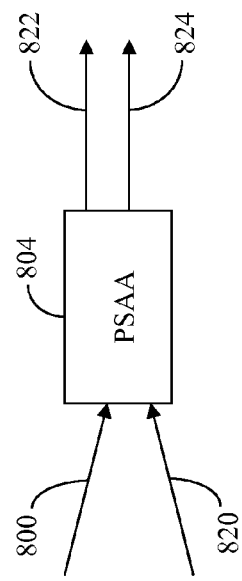
FIG. 8D is a schematic representation of an implementation of the Piecewise Stitching Algorithm according to one embodiment of the invention.

Referring to FIG. 8D, an embodiment utilizing the PSAA with multiple signals having related components, in absence of a CPR reference signal 802, is presented. Where a CPR reference signal 802 is not available, two or more signals corrupted with motion artifacts as a result of CPR are fed to the PSAA 804. For example, an ECG signal 800 and a Hemodynamic signal 820 may be inputted to the PSAA 804. In these embodiments, the PSAA 804 can correlate the signals and estimate the CPR artifact component. The PSAA 804 will then eliminate the CPR artifact component from original source signals and output clean versions of the input signals 822 along with a signal representing an estimate of the CPR artifact 824.

Figure 9:
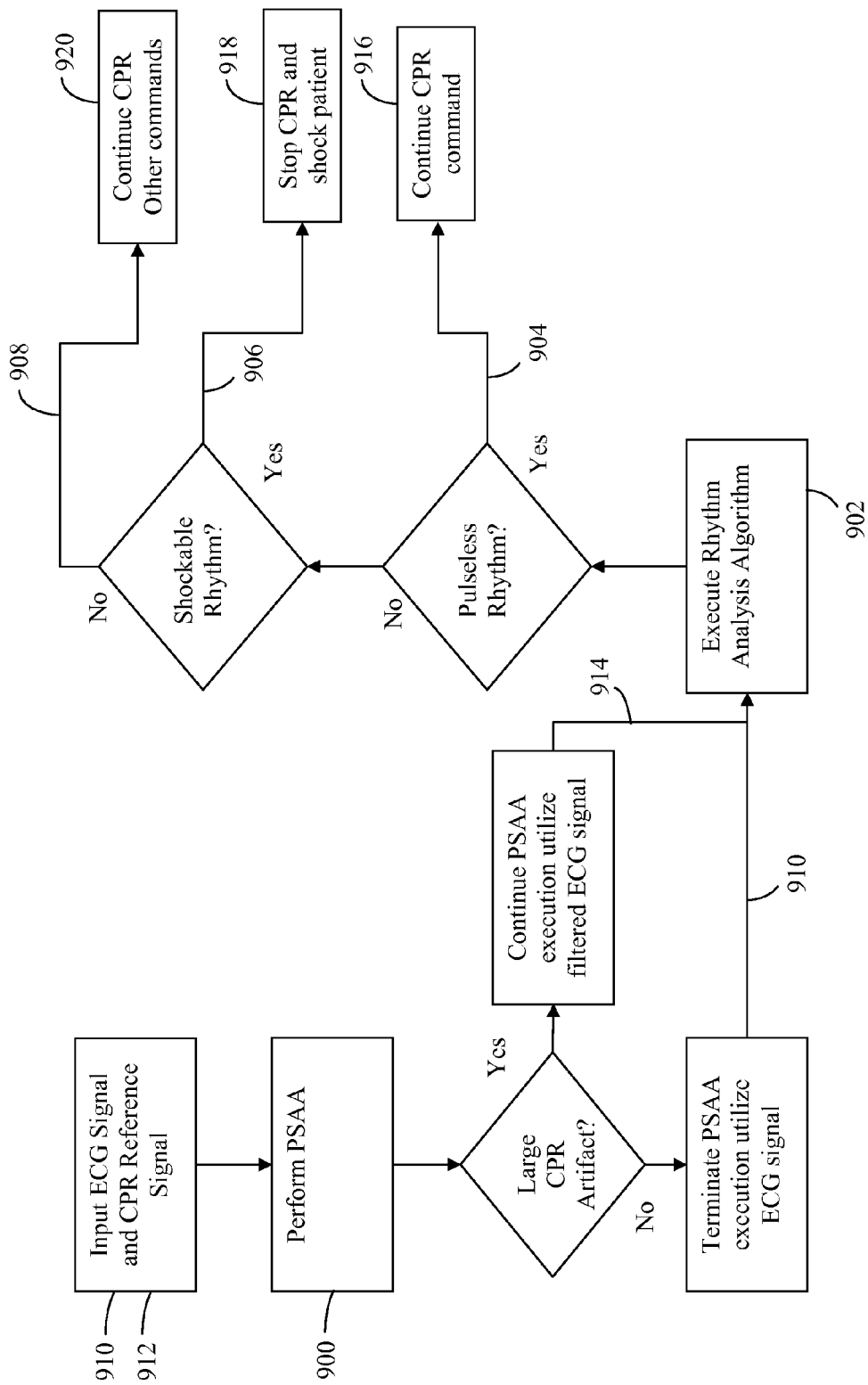
FIG. 9 is a schematic representation of the Piecewise Stitching Algorithm integrated into a defibrillator according to one embodiment of the invention.

In various embodiments, the PSAA may be also be utilized in AED systems to enable first-responder instruction based on states of sensed signals as shown in FIG. 9. For example, the PSAA 900 may be utilized in conjunction with a rhythm analysis algorithm 902 to determine between pulseless rhythm 904, shockable rhythm 906 and non-shockable rhythm 908.

In various embodiments, a pulseless rhythm 904 requiring continued CPR can be determined in AEDs utilizing the PSAA 900. In these situations, the PSAA 900 continually monitors the ECG signal 910 and CPR reference signal 912 and passes the clean ECG output signal 914 to a rhythm analysis algorithm 902 also implemented in the AED. The rhythm analysis algorithm 902 may then determine that continued CPR is required due to pulseless electrical activity or asystole and may instruct the AED to deliver the continue CPR command 916 to the first-responder.

Presence of a shockable rhythm 906 requiring CPR to cease and a shock applied may be made near real-time in an AED utilizing the PSAA 900. In these situations the PSAA 900 continually monitors the ECG signal 910 and CPR reference signal 912 and passes the clean ECG output signal 914 to the rhythm analysis algorithm 902. The rhythm analysis algorithm 902 may then determine that an electrical shock is required and may instruct the AED to deliver the stop CPR and shock patient command 918 as per protocol. In this way, the PSAA 900 may drive the interruption of CPR in order to provide treatment adhering to protocol. Various embodiments allow for control signals to be directed to mechanical compression devices delivering automatic CPR compressions in order to automatically synchronize the electrical shock and compression cycles. If there is a non-shockable rhythm, the AED may deliver the continue CPR command and other commands 920.

In certain embodiments, AEDs utilize the PSAA 900 to determine which signal processing is required by the PSAA 900. In these embodiments, the PSAA 900 outputs the sensed ECG signal in situations where the estimated artifact signal 916 exhibits low signal amplitude or situations where the artifact has marginal impact on the ECG signal 910. Thus, in these situations, the sensed ECG signal 910 may be utilized and passed directly to the rhythm analysis algorithm 902 bypassing the PSAA 900 signal processing thus further reducing latency and required processing power.

Figure 10A:
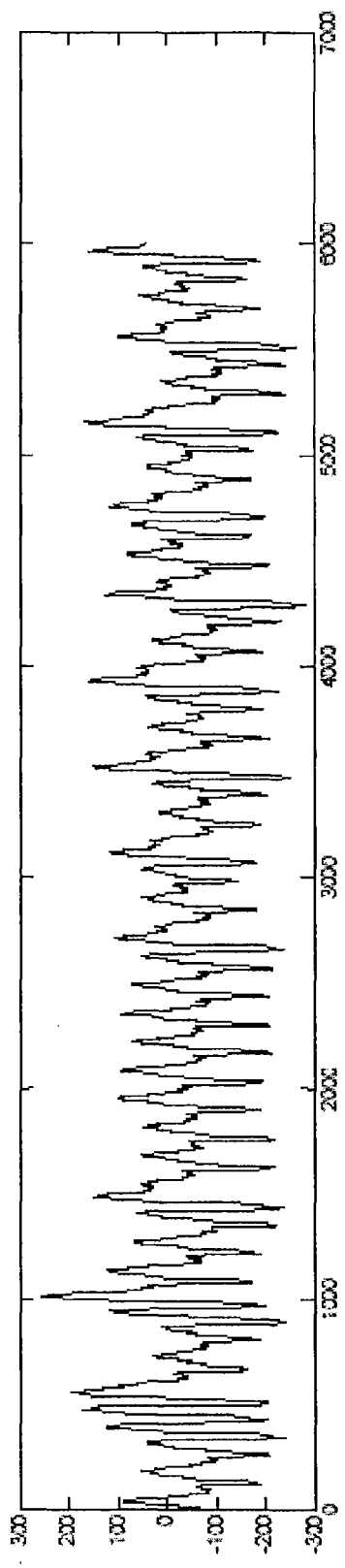
FIG. 10A is a graphical depiction of a ventricular tachycardia wave form corrupted with CPR artifacts.
Figure 10B:
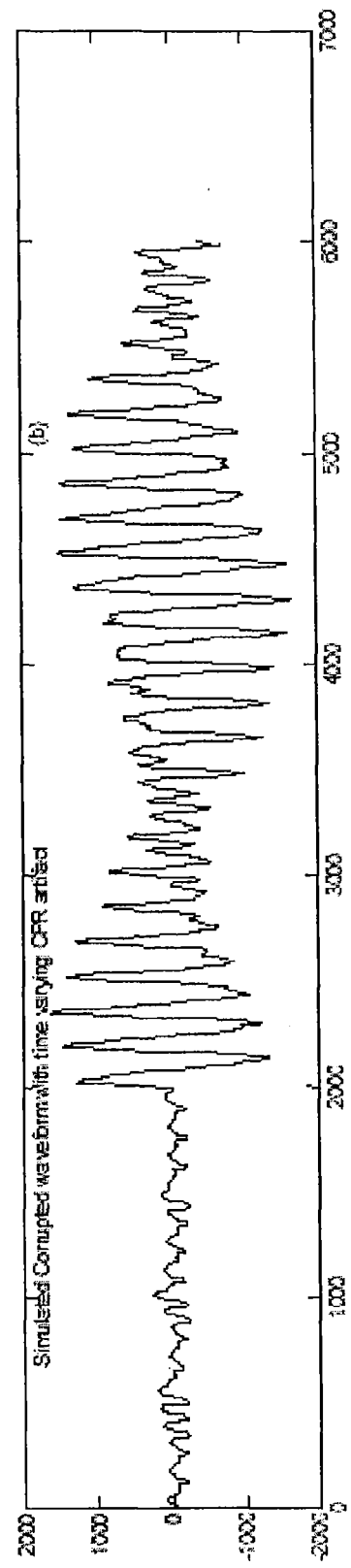
FIG. 10B is a graphical depiction of corruption and noise wave form.
Figure 10C:
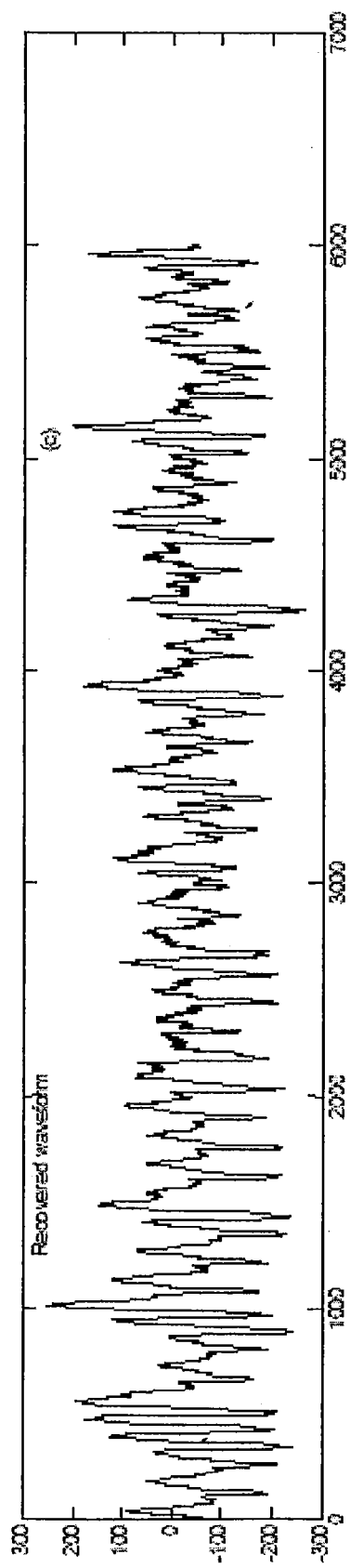
FIG. 10C is a graphical depiction of a recovered ventricular tachycardia wave form utilizing the Piecewise Stitching Algorithm according to one embodiment of the invention.

By implementing the PSAA and utilizing a CPR reference signal, various embodiments can remove noise from a sensed signal when signal to noise ratios show very large variations. For example, the PSAA algorithm can efficiently delineate artifacts even for severe artifact conditions where signal-to-noise ratios are 1 to 20, and in cases of asystole, this ratio can be much larger of the order of 1:1000, being restricted mainly by inherent noise characteristics of ECG channel. In this way, in various embodiments, the PSAA is able to analyze the sensed signal as shown in FIG. 10A and the CPR reference signal as shown in FIG. 10B and separate the CPR artifact resulting in a recovered ECG signal as shown in FIG. 10C. As mentioned above, in various other embodiments, the PSAA may perform the same analysis on various alternate primary and secondary signals to the same effect. Thus, for example, various signals that interfere with stress ECG machines and EEG machines may be removed by utilizing the PSAA.

Figure 11:
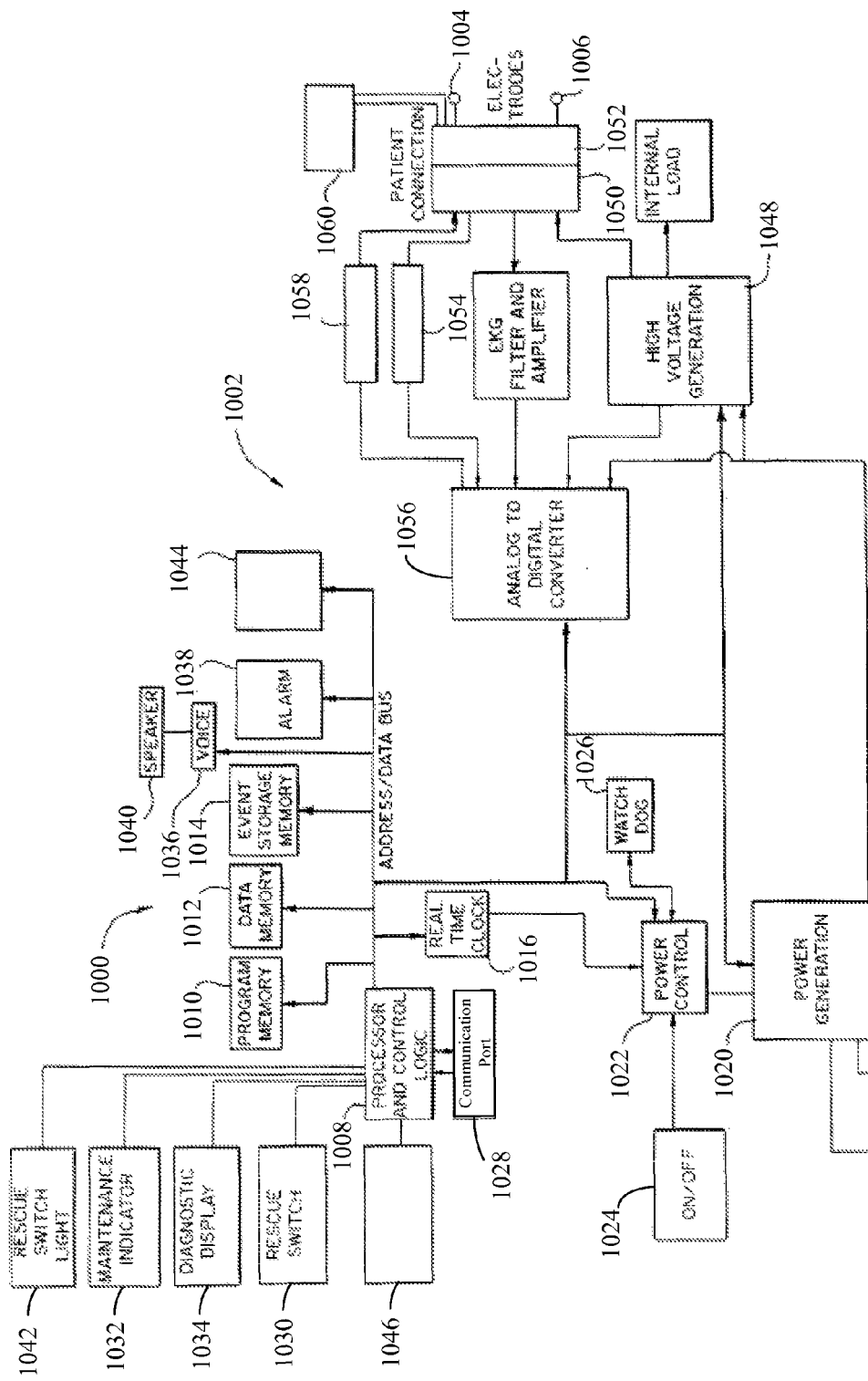
FIG. 11 is a schematic representation of an Automatic External Defibrillator utilizing the Piecewise Stitching Adaptive Algorithm according to one embodiment of the invention.

Now referring to FIG. 11, a block diagram of an AED 1000 implementing the PSAA according to one embodiment of the invention is presented. A digital microprocessor-based control system 1002 is used for controlling overall operation of AED 1000. The electrical control system 1000 further includes an impedance measuring circuit for testing the interconnection and operability of electrodes 1004 and 1006. Control system 1002 includes a processor 1008 interfaced to program memory 1010, data memory 1012, event memory 1014 and real time clock 1016. The operating program executed by processor 1008 is stored in program memory 1010. Electrical power is provided by the battery 1018 and is connected to power generation circuit 1020.

Power generation circuit 1020 is also connected to power control unit 1022, lid switch 1024, watch dog timer 1026, real time clock 1016 and processor 1008. A data communication port 1028 is coupled to processor 1008 for data transfer. In certain embodiments, the data transfer may be performed utilizing a serial port, usb port, firewire, wireless such as 802.11x or 3G, radio and the like. Rescue switch 1030, maintenance indicator 1032, diagnostic display panel 1034, the voice circuit 1036 and audible alarm 1038 are also connected to processor 1008. Voice circuit 1036 is connected to speaker 1040. In various embodiments, rescue light switch 1042 and a visual display 1044 is connected to the processor 1008 to provide additional operation information.

In certain embodiments, the AED will have a processor 1008 and a PSAA co-processor 1046. The PSAA co-processor 1046 may be the PSAA algorithm implemented in hardware and operably connected to the processor over a high-speed data bus. In various embodiments, the processor 1018 and PSAA co-processor 1046 are on the same silicon and may be implemented in a multi-core processor. Alternatively, the processor 1008 and PSAA co-processor may be implemented as part of a multi-processor or even networked processor arrangement. In these embodiments, the processor 1018 offloads some of the PSAA calculations to the PSAA co-processor thus optimizing the processing of the sensed signals from the electrodes 1004 and 1006. In other embodiments, the processor 1008 is optimized with specific instructions or optimizations to execute PSAA calculations. Thus, processor 1010 may execute PSAA calculations in fewer clock cycles and while commanding fewer hardware resources. In other embodiments, the logic and algorithm of the control system 1002 may be implemented in logic, either hardware in the form of an ASIC or a combination in the form of an FPGA, or the like.

High voltage generation circuit 1048 is also connected to and controlled by processor 1008. High voltage generation circuit 1048 may contain semiconductor switches (not shown) and a plurality of capacitors (not shown). In various embodiments, connectors 1050, 1052 link the high voltage generation circuit 1048 to electrodes 1004 and 1006.

Impedance measuring circuit 1054 is connected to both connector 1050 and real time clock 1016. Impedance measuring circuit 1054 is interfaced to real time clock through analog-to-digital (A/D) converter 1056. Another impedance measuring circuit 1058 may be connected to connector 1050 and real time clock 1016 and interfaced to processor 1008 through analog-to-digital (A/D) converter 1056. A CPR device 1060 may be connected to the processor 1008 and real time click 1016 through connector 1052 and A/D 1056. The CPR device 1060 may be a chest compression detection device or a manual automatic or semi-automatic mechanical chest compression device.

It should also be appreciated that the exemplary embodiment or exemplary embodiments are only examples, and are not intended to limit the scope, applicability, or configuration of the invention in any way. Rather, the foregoing detailed description will provide those skilled in the art with an enabling disclosure for implementing the exemplary embodiment or exemplary embodiments. It should be understood that various changes can be made in the function and arrangement of elements without departing from the scope of the invention as set forth in the appended claims and the legal equivalents thereof.

The embodiments above are intended to be illustrative and not limiting. Additional embodiments are within the claims. In addition, although aspects of the present invention have been described with reference to particular embodiments, those skilled in the art will recognize that changes can be made in form and detail without departing from the spirit and scope of the invention, as defined by the claims.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 212, sixth paragraph of 35 U.S.C. are not to be invoked unless the specific terms "means for" or "step for" are recited in a claim.

The invention claimed is:

1. An apparatus for filtering artifacts from ECG signals in real-time comprising:
   means for sensing an ECG signal, the ECG signal representing a physical impulse of cardiac tissue;
   means for sensing an artifact signal, the artifact signal representing a physiological function;
   means for removing the artifact signal from the ECG signal using a piecewise stitching adaptive algorithm that provides self-corrective, self-deconvolved, time-varying, self-adaptive signal estimation including analysis of overlapped adjacent segments that form a plurality of sample windows of the ECG signal and are stitched together with the artifact signal removed in response to the piecewise stitching adaptive algorithm.

2. An apparatus for filtering artifacts from ECG signals in real-time comprising:
   means for sensing an ECG signal, the ECG signal representing a physical impulse of cardiac tissue;
   means for sensing an artifact signal, the artifact signal representing a physiological function;
   means for removing the artifact signal from the ECG signal using a piecewise stitching adaptive algorithm that provides time-varying, self-adaptive signal estimation;
   wherein the piecewise stitching adaptive algorithm comprises:
   means for selecting signal sample windows from the ECG signal and the artifact signal;
   means for generating a primary ECG signal segment from the ECG signal and a primary artifact signal segment from the artifact signal based on the selected sample windows;
   means for determining a relationship between the primary ECG signal segment and primary artifact signal segment;
   means for estimating a ECG signal artifact in the primary ECG signal segment based on the determined relationship;
   means for removing the estimated ECG signal artifact from the primary signal segment of the ECG signal.

3. An apparatus having a processor adapted to filter CPR compression artifacts from ECG signals in real-time comprising:
   an ECG sensor for sensing a ECG signal representing a physical impulse of cardiac tissue;
   an artifact sensor for sensing an artifact signal representing a physiological function;
   a piecewise stitching adaptive algorithm processor coupled to the ECG sensor and the artifact sensor programmed to calculate a ECG signal artifact created by the artifact signal and to remove the ECG signal artifact from the ECG signal utilizing self-corrective, self-deconvolved, time-varying, self-adaptive signal estimation including analysis of overlapped adjacent segments that form a plurality of sample windows of the ECG signal and are stitched together with the artifact signal removed in response to the piecewise stitching adaptive algorithm.

4. An apparatus having a processor adapted to filter CPR compression artifacts from ECG signals in real-time comprising:
   an ECG sensor for sensing a ECG signal representing a physical impulse of cardiac tissue;
   an artifact sensor for sensing an artifact signal representing a physiological function;
   a piecewise stitching adaptive algorithm processor coupled to the ECG sensor and the artifact sensor programmed to calculate a ECG signal artifact created by the artifact signal and to remove the ECG signal artifact from the ECG signal utilizing time-varying, self-adaptive signal estimation;
   wherein the piecewise stitching processor is adapted to execute instructions stored in a memory operably coupled to the piecewise stitching processor, the instructions comprising:
   selecting signal sample windows from the ECG signal and the artifact signal;
   generating a primary ECG signal segment from the ECG signal and a primary artifact signal segment from the artifact signal;
   determining a relationship between the primary ECG signal segment and primary artifact signal segment;
   estimating a signal artifact in the primary signal based on the determined relationship;
   removing the estimated signal artifact from the primary signal segment.

5. A machine-implemented method for filtering signal artifacts from an ECG signal in real-time comprising:
   sensing, with an ECG sensor, an ECG signal representing a physical impulse of cardiac tissue;
   sensing, with an artifact sensor, an artifact signal representing physiological function;
   using a piecewise stitching adaptive algorithm providing self-corrective, self-deconvolved, time-varying, self-adaptive signal estimation including analysis of overlapped adjacent segments that form a plurality of sample windows of the ECG signal and are stitched together with the artifact signal removed in response to the piecewise stitching adaptive algorithm executed by a processor coupled to the ECG sensor and the artifact sensor to automatically remove the artifact signal from the ECG signal to generate a clean ECG signal.

6. A machine-implemented method for filtering signal artifacts from an ECG signal in real-time comprising:
   sensing, with an ECG sensor, an ECG signal representing a physical impulse of cardiac tissue;
   sensing, with an artifact sensor, an artifact signal representing physiological function;
   using a piecewise stitching adaptive algorithm providing time-varying, self-adaptive signal estimation executed by a processor coupled to the ECG sensor and the artifact sensor to automatically remove the artifact signal from the ECG signal to generate a clean ECG signal;

wherein the piecewise stitching adaptive algorithm comprises:

selecting a first signal sample window from the ECG signal and a second signal sample window from the artifact signal;

generating a primary ECG signal segment from the first signal sample window and a primary artifact signal segment from the second signal sample window;

determining a relationship between the primary ECG signal segment and the primary artifact signal segment;

estimating a signal artifact in the primary ECG signal segment based on the relationship;

removing the signal artifact from the primary ECG signal segment.

7. The method of claim 5 further comprising using a rhythm analysis algorithm processor to identify shockable ECG rhythm.

8. The method of claim 5 wherein sensing, with an artifact sensor, an artifact signal representing a physical impulse initiates the processor to automatically remove the signal artifact from the ECG signal using a piecewise stitching adaptive algorithm.

9. The method of claim 6 wherein selecting the first signal sample window from the ECG signal and the second signal sample window from the artifact signal further comprises selecting a signal sample window selected form the group consisting of uniform and non-uniform sized signal sample windows depending on a time delay between the ECG signal and the artifact signal.

10. The method of claim 6 wherein selecting the first signal sample window from the ECG signal and the second signal sample window from the artifact signal further comprises selecting the first and second signal sample windows using matching start and end times.

11. The method of claim 6 wherein selecting the first signal sample window from the ECG signal and the second signal sample window from the artifact signal further comprises selecting the first and second signal sample windows using non-matching signal sample window start and signal sample window end times.

12. The method of claim 6 wherein selecting the first signal sample window from the ECG signal and the second signal sample window from the artifact signal further comprises utilizing a scheme to indicate a signal sample window start time and a signal sample window end time selected from the group consisting of adaptive indexing and segment-by-segment regression.

13. The method of claim 6 wherein selecting the first signal sample window from the ECG signal and the second signal sample window from the artifact signal further comprises auto correlating the ECG signal and the artifact signal, cross correlating the ECG signal and the artifact signal and utilizing an adaptive indexing scheme to determine a signal sample window start time and a signal sample window end time.

14. The method of claim 5 wherein using a piecewise stitching adaptive algorithm processor coupled to the ECG sensor and the artifact sensor to automatically remove the signal artifact from the ECG signal using a piecewise stitching adaptive algorithm further comprises:

estimating a phase lead or a phase lag between the ECG signal and the artifact signal using a shifted autocorrelation calculation wherein the phase lead or the phase lag calculation is stored in a memory for selecting additional signal sample windows.

15. The method of claim 5 using a piecewise stitching adaptive algorithm processor coupled to the ECG sensor and the artifact sensor to automatically remove the signal artifact from the ECG signal using a piecewise stitching adaptive algorithm further comprises:

weighting primary and secondary signal segments with a weighting scheme selected from the group consisting of equal weighting and central segment weighting.

16. The method of claim 5, wherein the artifact signal is selected from the group consisting of a CPR compression signal and a hemodynamic signal.

17. The method of claim 5, wherein an artifact representative CPR signal is generated by applying a bandpass filter to the ECG signal.

18. The method of claim 5, wherein the artifact signal is graded using a time domain estimation to generate a grade, wherein the time domain estimation is selected from the group consisting of zero-crossings and peak-to-peak oscillations.

19. The method of claim 18, wherein the grade indicates the quality of the signal-to-noise ratio and provides a confidence measure for further rhythm identification.

20. The method of claim 6, further comprising de-noising the ECG signal and the artifact signal.

21. The method of claim 6 further comprising generating mean values of the ECG signal and artifact signal wherein the mean values are updated every signal sample window.

22. The method of claim 13 wherein the autocorrelation of the artifact signal and the cross correlation of the artifact signal and the ECG signal are updated every signal sample window.

23. The method of claim 13 wherein the autocorrelation of the artifact signal and the cross correlation of the artifact signal and the ECG signal are computed at selected signal sample windows based on a specified signal sample window length and signal sample window overlap.

* * * * *